United States Patent
King, Jr. et al.

(10) Patent No.: US 11,460,462 B2
(45) Date of Patent: Oct. 4, 2022

(54) MICROANALYSIS OF FINE GRAINED ROCK FOR RESERVOIR QUALITY ANALYSIS

(71) Applicant: ExxonMobil Upstream Research Company, Spring, TX (US)

(72) Inventors: Hubert E. King, Jr., Flemington, NJ (US); Michael G. Myers, Lebanon, NJ (US); William A. Lamberti, Stewartsville, NJ (US); Antonio S. Buono, Spring, TX (US); James H. Macquaker, The Woodlands, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 70 days.

(21) Appl. No.: 16/552,201

(22) Filed: Aug. 27, 2019

(65) Prior Publication Data

US 2020/0132657 A1 Apr. 30, 2020

Related U.S. Application Data

(60) Provisional application No. 62/753,566, filed on Oct. 31, 2018.

(51) Int. Cl.
*G01N 33/24* (2006.01)
*G01N 15/08* (2006.01)
(Continued)

(52) U.S. Cl.
CPC ......... *G01N 33/241* (2013.01); *G01N 15/088* (2013.01); *G01N 23/203* (2013.01);
(Continued)

(58) Field of Classification Search
CPC ........... G01N 15/088; G01N 2223/418; G01N 2223/616; G01N 23/203; G01N 33/24;
(Continued)

(56) References Cited

U.S. PATENT DOCUMENTS 8,967,249 B2 3/2015 Akkurt et al.
2012/0197526 A1* 8/2012 Leyte Guerrero ..... G01N 23/04
250/311

(Continued)

FOREIGN PATENT DOCUMENTS

CN 105 334 149 A 2/2016
EP 1938281 B1 1/2015

OTHER PUBLICATIONS

Gucsik et al. (2003) "Scanning electron microscopy, cathodoluminescence, and Raman spectroscopy of experimentally shock-metamorphosed quartzite", Meteoritics & Planetary Science 38, No. 8, pp. 1187-1197.

(Continued)

*Primary Examiner* — Bobbak Safaipour
(74) *Attorney, Agent, or Firm* — ExxonMobil Upstream Research Company—Law Department (57) ABSTRACT

A method of analyzing a rock sample includes analyzing one or more large-area, low-resolution micrographs to identify areas requiring higher-resolution imaging, and selecting one or more analysis regions from the areas requiring higher-resolution imaging. Multi-spectral imaging is used on the one or more analysis regions to obtain one or more high-resolution, multi-spectral images, and one or more features of the rock sample are identified from the corresponding one or more high-resolution, multi-spectral images. The method further includes upscaling the one or more high-resolution, multi-spectral images and thereby geo-locating the features of the rock sample to key regions of the rock sample.

16 Claims, 6 Drawing Sheets

(51) Int. Cl.
*G01N 23/203* (2006.01)
*G06T 7/00* (2017.01)

(52) U.S. Cl.
CPC .. *G06T 7/0004* (2013.01); *G06T 2207/10056* (2013.01); *G06T 2207/30181* (2013.01)

(58) Field of Classification Search
CPC ........ G01N 33/241; G06T 2207/10056; G06T 2207/10061; G06T 2207/30181; G06T 7/0002; G06T 7/0004
See application file for complete search history.

(56) References Cited

U.S. PATENT DOCUMENTS

| | | | |
|---|---|---|---|
| 2013/0257424 A1 | 10/2013 | Holland et al. | |
| 2013/0259190 A1* | 10/2013 | Walls | G01N 33/2823 382/109 |
| 2015/0355158 A1 | 12/2015 | Lander et al. | |
| 2016/0305820 A1* | 10/2016 | Zollars | G01J 3/0216 |
| 2016/0307312 A1* | 10/2016 | Sungkorn | G06V 10/462 |
| 2016/0349174 A1 | 12/2016 | Washburn | |
| 2017/0108483 A1* | 4/2017 | Clark | G01N 33/24 |
| 2017/0143854 A1* | 5/2017 | Chen | C01G 49/0063 |
| 2018/0327651 A1* | 11/2018 | Piri | C09K 8/18 |
| 2018/0328905 A1* | 11/2018 | Jacobi | G01N 33/241 |
| 2020/0132657 A1* | 4/2020 | King, Jr. | G01N 33/24 |

OTHER PUBLICATIONS

Mayhew et al. (2018) "Iron transformations during low temperature alteration of variably serpentinized rocks from the Samail ophiolite, Oman", Geochimica et Cosmochimica Acta, Pergamon Press, New York, NY, vol. 222, pp. 704-728.

Yang et al. (2017) "Nanoscale geochemical and geomechanical characterization of organic matter in shale", Nature Communications, vol. 8, No. 1, pp. 1-9.

Kotula, P. G. et al. (2006) *"Tomographic Spectral Imaging with Multivariate Statistical Analysis: Comprehensive 3D Microanalysis"*, Microscopy and Microanalysis, Issue 12, pp. 36-48.

Kotula, P. G. et al. (2006) *"Application of Multivariate Statistical Analysis to STEM X-ray Spectral Images: Interfacial Analysis in Microelectronics"*, Microscopy and Microanalysis, Issue 12, pp. 538-544.

Anders et al. (2014) *"Microfractures: A Review"*, Journal of Structural Geology, vol. 69, Part B, Dec. 2014, pp. 377-394.

Hiatt et al. (2014) *"A Review of Applications for Understanding Diagenesiss, Reservoir Quality, and Pore System Evolution"*, Cathodoluminescence Petrography of Carbonate Rocks, Mineralogical Association of Canada Short Course 45, Frederiction NB, May 2014, pp. 75-96.

Lai et al. (2017) *"Origin and Distribution of Carbonate Cement in Tight Sandstones: The Upper Triassic Yanchang Formation Chang 8 Oil Layer in West Ordos Basin, China"*, Geofluids, vol. 2017, July, pp. 1-13.

* cited by examiner

MICROANALYSIS OF FINE GRAINED ROCK FOR RESERVOIR QUALITY ANALYSIS

CROSS-REFERENCE TO RELATED APPLICATION

This application claims the benefit of U.S. Provisional Application No. 62/753,566 entitled "Microanalysis of Fine Grained Rock for Reservoir Quality Analysis" that was filed on Oct. 31, 2018, the disclosure of which is incorporated herein by reference.

BACKGROUND

The productivity of reservoir rocks is related to many rock properties, among them porosity, the composition of pore lining materials, and mineral fabric. These features are commonly examined by optical microscopy for conventional rocks, which provides a favorable alignment between high enough resolution to image the pore lining materials (e.g., few micrometers scale) as well as the laminae fabric variability (e.g., millimeter scale). As a result, optical microscopy of thin sections is a mainstay of geology.

Fine-grained rocks, such as mudstones, however, present a significant challenge. In mudstones, for instance, mineral grains and the intervening cements and associated pores are present in the micrometer to sub-micrometer range, which is well below optical resolution. Nonetheless, mudstone bedding and laminae scale variability are also important, and these features exist at millimeter scales that typically require large-area analysis. The fine-grained nature of the constituent phases of mudstones and their varying origin is crucial when they are being considered as targets for optimizing recovery engineering strategies and defining their performance as hydrocarbon source rocks and seals. Knowledge of the mineral type and distribution at various length scales, along with the spatial relationships between grains, is fundamental to developing these engineering strategies.

Imaging techniques can span many decades in size, but co-locating (e.g., geo-locating) high-resolution images within larger area, lower-resolution images can be difficult. To draw more accurate conclusions about reservoir quality, there is a need for large area, high-resolution ("fine-resolution") rock imaging. There is also a need to account for rock structure at several scales.

Background references may include European Patent No. 1938281 B1, U.S. Pat. No. 8,967,249, and U.S. Patent Application Publication Nos. 2013/0257424 and 2015/0355158. Additional background references may also include Anders et al., "Microfractures: A Review", *Journal of Structural Geology*, Vol. 69, Part B, pp. 377-394 (2014); Hiatt et al., "A Review of Applications for Understanding Diagenesiss, Reservoir Quality, and Pore System Evolution", *Cathodoluminescence Petrography of Carbonate Rocks*, Mineralogical Association of Canada Short Course 45, pp. 75-96 (2014); and Lai et al., "Origin and Distribution of Carbonate Cement in Tight Sandstones: The Upper Triassic Yanchang Formation Chang 8 Oil Layer in West Ordos Basin, China", *Geofluids*, Volume 2017, p. 1-13 (2017).

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to petrography and, more particularly, to large-area microanalysis for fine-grained rocks.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

Capturing the small-scale variability in a rock sample, while simultaneously determining and analyzing larger-scale variability can prove advantageous. The methods described herein help facilitate examination of large-scale texture components and structural and compositional trends of the rock simultaneously with very small features of the rock provided through high-resolution data. More specifically, embodiments of the present disclosure address the challenge of high-spatial resolution and extended area analysis in petrographic evaluation for fine-grained rocks, such as mudstones, which host abundant supplies of tight oil and shale gas reservoirs. For fine-grained rocks, it can be advantageous to determine the type and distribution (location) of grains and the location of pores present therein. Some grains are reactive and dissolve over time to cement adjacent grains together, but dissolution sometimes makes holes in the rock, thus resulting in intragranular porosity.

The presently disclosed methods help an analyst determine where the grains are, which grains are actual grains, which grains are instead cement, and what the porosity is located relative to grain and cement distribution. Understanding such features of a rock is important as porosity equates to hydrocarbon storage capacity, and once the characteristics and chemistry of the grains are determined, an informed determination of how the rock will respond to hydraulic fracturing may be made. As will be appreciated, this may lead to improved estimates of the quality of rock resources for oil and gas extraction.

With any petrographic imaging method, an analyst (e.g., a geologist) must define what rock features are important to image and what signal type can highlight those features. Additionally, the analyst must balance between information content, acquisition time, analysis time, and data file size. In analyzing fine-grained rocks, the methods described herein utilize various imaging methods including, but not limited to, optical microscopy imaging, backscattered electron imaging ("BSI"), elemental imaging via both energy dispersive x-ray spectroscopy ("EDS") and wavelength dispersive x-ray spectroscopy ("WDS"), and spectrally-resolved cathodoluminescence ("CL"). Resulting data sets can be hyperspectral in nature, with full EDS and CL spectra obtained at each pixel, along with intensity information from electron detectors, optical microscopy, and WDS. Through spatial correlation (i.e., geo-locating) of these data, a rich description of the rock under study emerges. These data are particularly useful for elucidating porosity types and evolution through diagenesis.

Analysis of fine-grained rock tight reservoirs shows there is a significant compositional and grain origin variability visible at pore, lamina, and bed scales. These differences are controlled by varying starting compositions of the constituent as well as differences in the subsequent fluid flux through the different layers. This variability means that upscaling from small field of view (i.e., very high resolution), to optical thin section (i.e., large-area, low-resolution microscopy), to core, to well performance, without knowledge of the variability between the component elements, is almost impossible. In contrast, the presently described methods facilitate upscaling of high-resolution, multi-spectral images and relying on geolocation to place the high-resolution data into a broader context through linkage to larger-scale features of a rock sample.

According to methods described herein, a petrographic analyst (i.e., a geologist) may first identify and select key regions of a rock sample that have one or more attributes of interest. The rock sample may comprise a hand specimen sized sample of a fine-grained rock obtained from a geological region of interest. In some cases, the sample may originate from a downhole core sample obtained via a subsurface sampling operation. In other cases, the rock sample may alternatively comprise an exposure sample obtained from a surface location (e.g., an open quarry or the like). Example attributes of interest identifiable by the geologist in selecting key regions include the formation name, key mineral contents (e.g., quartz, carbonate, solid organic concentrations, etc.), spatial distribution of mineral phases and their composition within the sample (e.g., grans versus cement), fabrics visible (e.g., ripples, parallel bedding, etc.), grain origins, fossils present, organic carbon type, grain size of depositional components, depth in the well, porosity, and biostratigraphic context.

Once the key regions of the rock sample have been identified, one or more optical thin sections of the rock sample may be extracted at those key regions for further analysis. As used herein, the term "optical thin section" refers to a thin section (i.e., slice) of a rock sample suitable for performing light optical microscopy. The geologist may analyze the extracted optical thin sections of the rock sample using light optical large-area, low-resolution microscopy; high-resolution scanning on a computer scanner; confocal microscopy; fluorescence; and/or cathodoluminescence, and thereby obtain one or more large-area, low-resolution micrographs. These micrographs would typically show features that range from centimeters to micrometers in size. Example large-area, low-resolution microscopy technologies that may be used to obtain the large-area, low-resolution micrograph(s) include, but are not limited to, optical microscopy (also referred to as polarized light microscopy) and low magnitude (resolution) backscatter electron microscopy.

The large-area, low-resolution micrograph of each optical thin section may reveal particular mineralogical and fabric attributes of interest, or particular regions of the optical thin section where these attributes are (or might be) present. Some of the mineralogical and fabric attributes may comprise large-scale texture components identifiable by the geologist at the low-scale resolution. Since these features are identifiable, the petrographic analysis of these regions may be complete at this point and the data may be compiled for consideration. Other revealed texture components, however, may be present in the micrometer to sub-micrometer range, and thus may not be ascertainable at the large-area, low-resolution scale. Rather, such features may require higher-resolution imaging techniques to reveal their compositional and spatial distributions. Such texture components can include, for example, mineralogical and fabric attributes of the rock sample such as, but not limited to, mineral grains, presence of organic carbon, intervening cements, and associated pores (e.g., intragranular porosity, grain dissolution porosity, fracture porosity, and/or intercrystalline porosity).

Figure 1:
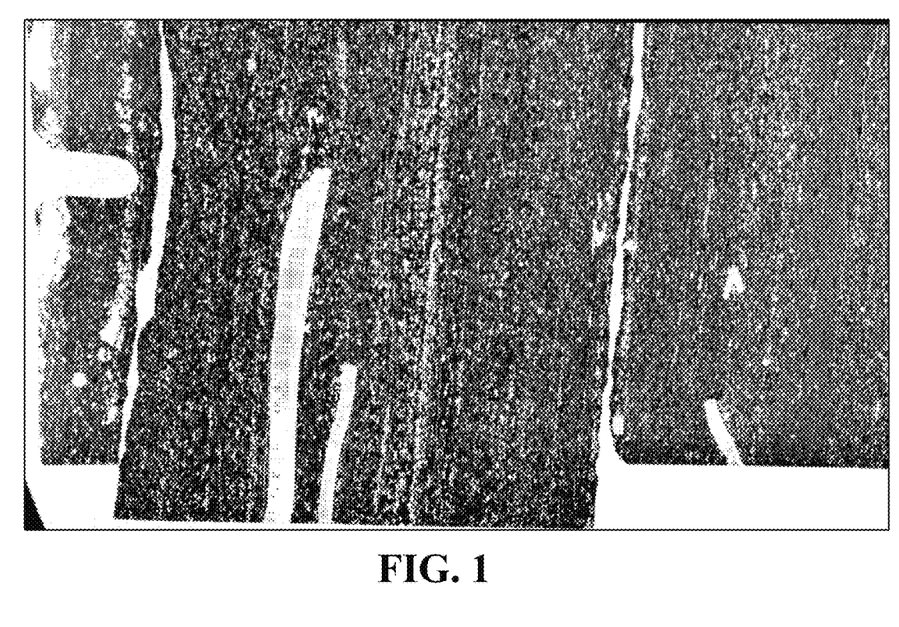
FIG. 1 is a transmitted light image taken from an example optical thin section.
Figure 2:
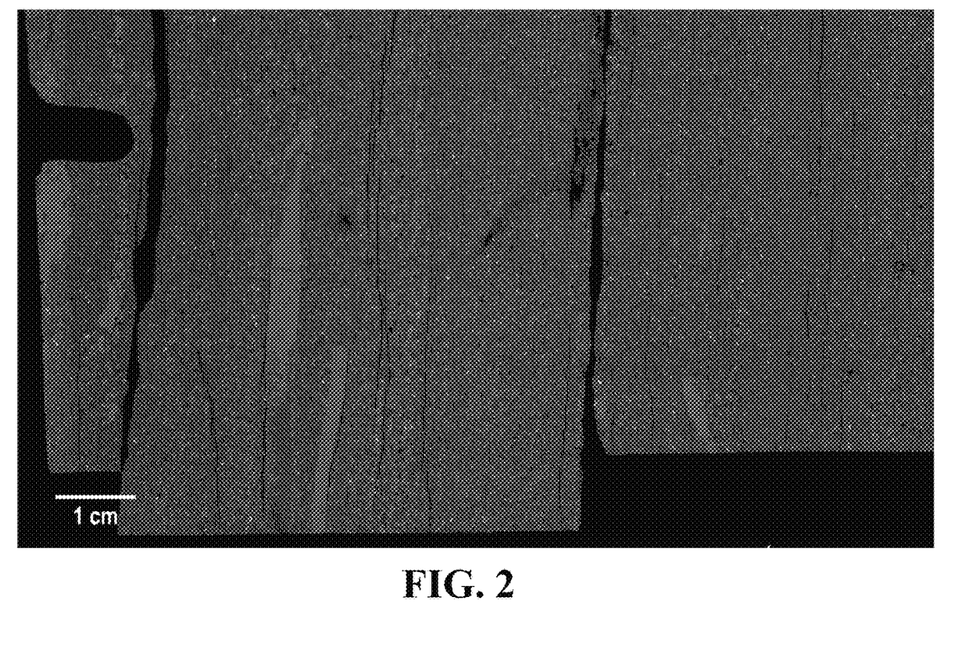
FIG. 2 is a backscatter electron micrograph image of the example optical thin section of FIG. 1 and at the same resolution as the transmitted light image of FIG. 1.

FIG. 1 is a transmitted light image (optical micrograph) taken from an example optical thin section of a rock sample, and FIG. 2 is a large-area, low-resolution backscatter electron micrograph image of the example optical thin section at the same resolution as FIG. 1, but providing atomic number contrast. The micrographs shown in FIGS. 1 and 2 are examples of large-area, low-resolution micrographs. As illustrated, the rock of the example optical thin section comprises a stacked succession of normally graded thin beds with disarticulated bivalve fragments that define the bedding planes. Individual beds are sharp-based and normally graded. Internally, the basal laminae are coarser and enriched in foraminifer tests and organized into planar partings, while the upper laminae are depleted in foraminifer, enriched in fecal pellet, contain some clay minerals, and exhibit a wavy discontinuous fabric.

At low magnification (i.e., thin section scale or lamina scale resolution), the two imaging methods of FIGS. 1 and 2 provide essentially similar data because there are no readily apparent large compositional changes in the sample dominated by fine-grained mineral mixtures of, for example, clays, calcite, quartz, kaolinite, and organic carbon. To image such fine-grained mineral mixtures requires higher resolution and/or use of additional contrast factors beyond simple backscattered electron intensity. As described herein, multi-scale and/or multi-method large-area imaging techniques coupled with small-area, high-resolution techniques may be used to obtain a fuller view of the cementations and stratigraphy than is allowed using large-area, low-resolution microscopy alone. Large-area imaging provides a much better picture of the overall structure and composition of the rock, removing some of the bias and allowing a geologist to more quantitatively describe the rock when coupled with small-area, high-resolution analyses. These advancements can link to stratigraphic variability in the rock, which allows a better understating on the controls of flow and hydraulic fracturing capabilities within tight reservoirs.

According to embodiments of the present disclosure, one or more analysis regions may be identified and selected from a large-area, low-resolution micrograph of an optical thin section of the rock sample, and such regions may be analyzed using a multi-spectral imaging mode (technology) to enable more detailed characterization of such regions and thereby build an integrated picture of what cannot be observed with large-area, low-resolution microscopy. By geo-locating images derived from multiple techniques across scales, a geologist is able to maintain spatial context with information derived from a suite of analytical methods. This may prove advantageous in helping a geologist determine and understand how the reservoir from where the rock sample originated is constituted (put together).

Figure 3:
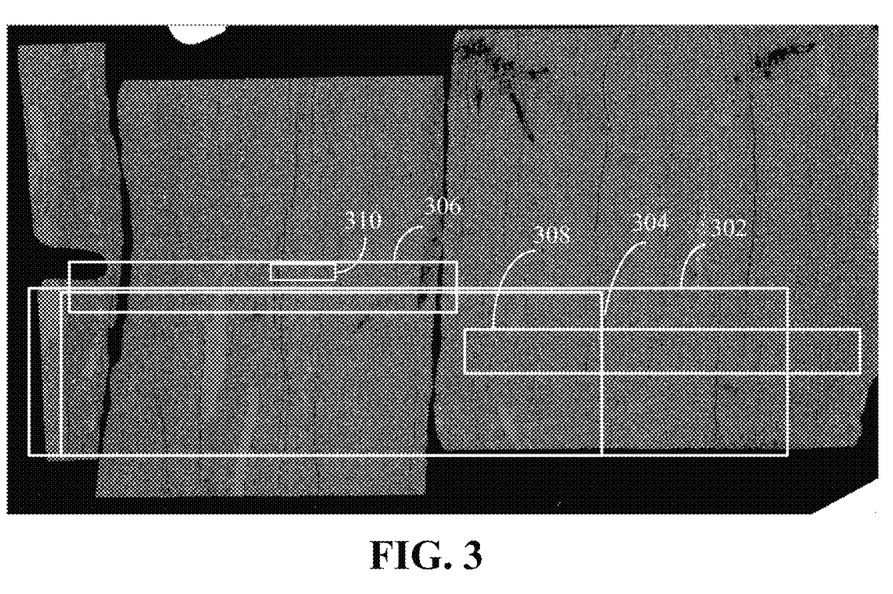
FIG. 3 is a larger view of the backscatter electron micrograph of FIG. 2 and outlines an example staged microanalysis strategy.

FIG. 3 is a larger view of the backscatter electron micrograph of FIG. 2 and outlines an example staged microanalysis strategy progressing from relatively large analysis regions at lower resolution, to smaller analysis regions at increasingly finer resolution. More specifically, a plurality of analysis regions have been identified for analysis at higher resolution imagery, depicted in FIG. 3 as a first analysis region 302, a second analysis region 304, a third analysis region 306, a fourth analysis region 308, and a fifth analysis region 310. Each analysis region 302 to 310 may be analyzed using multi-spectral imaging to obtain a corresponding high-resolution, multi-spectral image at pore/grain scale. The multi-spectral imaging may include non-spectral data as well as hyperspectral data. Example multi-spectral imaging technologies that may be used include, but are not limited to, high-resolution backscattered electron imaging, elemental imaging via both energy dispersive x-ray spectroscopy ("EDS") and wavelength dispersive x-ray spectroscopy ("WDS"), high resolution x-ray fine structure spectroscopy (e.g., soft x-ray emission spectroscopy), energy-filtered secondary electron imaging, backscattered electron imaging, spectrally-resolved cathodoluminescence ("CL"), panachromatic cathodoluminescent imaging, angle-resolved electron imaging, magnetic domain imaging, electron-induced acoustic imaging, electron beam induced charge imaging, electron diffraction based imaging, electron-induced infrared imaging, Fourier-transform infrared spectroscopy ("FTIR"), ultraviolet imaging, atomic force microscopy imaging, and acoustic microscopy imaging. Those skilled in the art will readily recognize that combining these or a subset of these methods (i.e., imaging techniques) opens up additional spectral windows that may significantly aid mineral identification and characterization.

In the depicted example, the size of the analysis regions 302 to 310 is indicative of the type of multi-spectral imaging used, the measurement time, and the computing power necessary to generate the corresponding high-scale micrograph (e.g., a quanta of data). The type of multi-spectral imaging may be selected, at least in part, by considering a desired image resolution, the time required to obtain the desired image resolution, and a maximum data set size. In some cases, there may be a trade-off between time and image quality, the longer the analysis (imaging) time, the higher the resulting resolution. In contrast, the shorter the analysis (imaging) time, the lower the resulting resolution. Moreover, another consideration may be potential damage to the sample that is caused by lengthening the analysis time as prolonged exposure of a sample to electron beams may physically damage the sample over time.

As the analysis regions 302 to 310 depicted in FIG. 3 get smaller, the resolution of the corresponding high-scale micrograph increases. For example, the first (and largest) analysis region 302 may be analyzed using EDS at a resolution of 5 micrometers (μm); the second analysis region 304 may be analyzed using EDS at a resolution of 3 μm; the third analysis region 306 may be analyzed using WDS and CL at a resolution of 5 μm; the fourth analysis region 308 may be analyzed using WDS and CL at a resolution of 5μm; and the fifth (and smallest) analysis region 310 may be analyzed using WDS and CL at a resolution of 1 μm.

Figure 4:
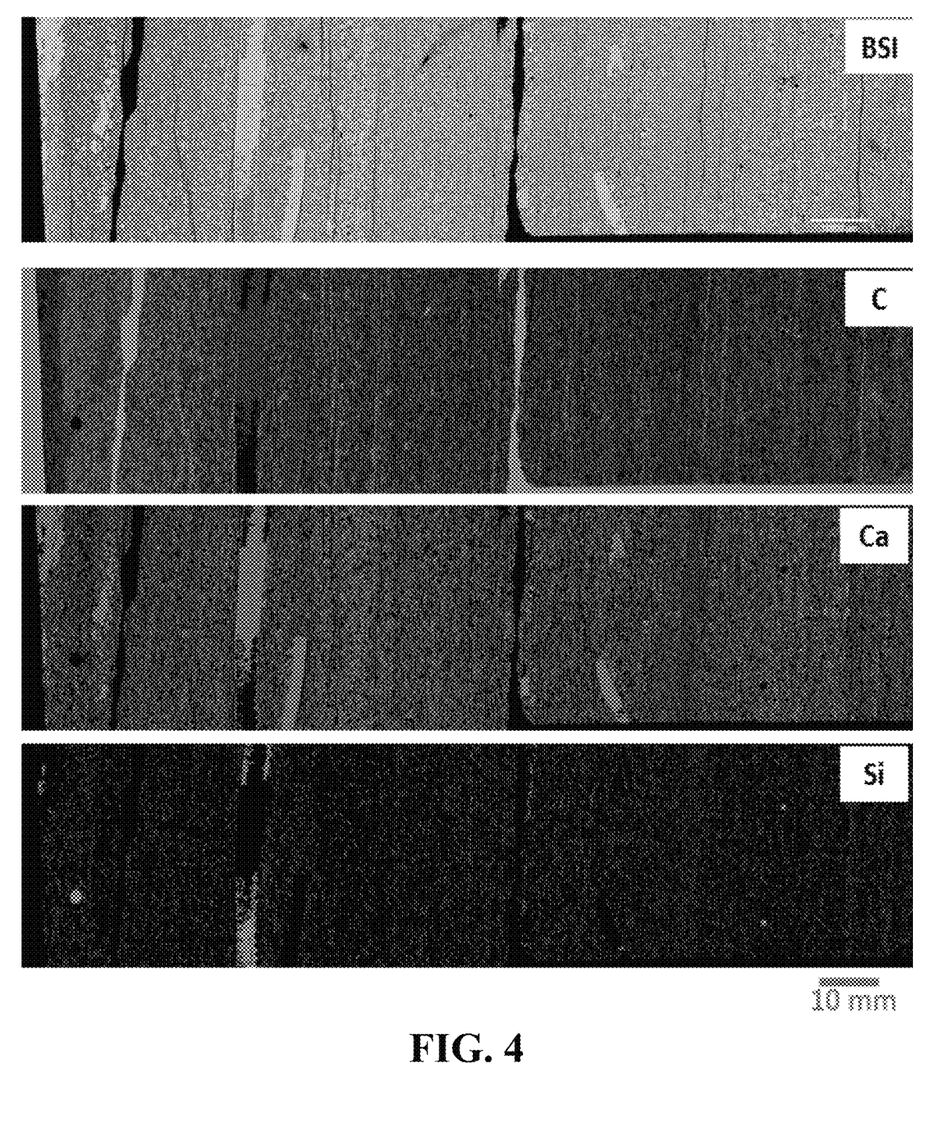
FIG. 4 depicts a backscattered electron image and corresponding compositional maps derived from analysis of the first analysis region of FIG. 3.

FIG. 4 depicts a backscattered electron image and corresponding compositional maps derived from high-resolution analysis of the first analysis region 302 of FIG. 3. More particularly, FIG. 4 depicts a high-resolution, multi-spectral image at pore/grain scale and separated out into specific image layers. Here, the resolution is chosen as required to reveal the features of interest. The details of this are determined by the particular area on the rock being studied and the type of microscopy used. The top (upper) image is a backscatter electron image ("BSI"), and the resulting multi-spectral image was then divided into individual atomic elements, e.g., carbon (C), calcium (Ca), and silicon (Si). The lighter and darker parts of each compositional map indicate the amount of that element at that location in the corresponding image. As will be appreciated, additional spectral images (chemical maps) may alternatively be obtained depending on the number and type of electron detectors used. Accordingly, the depicted multi-spectral images are provided for demonstration purposes only.

FIG. 4 demonstrates the value of coupling x-ray compositional information with backscattered electron and optical imaging to determine large-scale mineral distributions and mineral fabric. The images in FIG. 4 were created by forming elemental montages of one hundred sixty-eight (168) individual hyperspectral x-ray maps, each at 256×192 pixels. The resultant map size of each image is 6144×1344 pixels, representing 8.2 million x-ray spectra, and corresponding intensity data from the backscattered electron detector.

It is noted that the data represented by the images of FIG. 4 is produced in pixel sizes ranging from about 1 μm to about 5 μm. At the coarse resolutions depicted in FIG. 4, large variations in composition and fabric are visible. However, the actual data in FIG. 4 contains information at finer length scales than are depicted in the document image. This often reveals variability at finer length scales that would otherwise be lost. The context of this fine scale variability, in terms of fabric, or depositional processes (provenance) and differences in fluid flux (manifest as different cementing agents, varying porosity, etc.) through different regions of the sample, can be completely lost with less robust analytical approaches. This variability demonstrates the critical importance of placing the high-resolution, multi-spectral images into a broader context, a goal of geo-location to the original rock sample.

Figure 5:
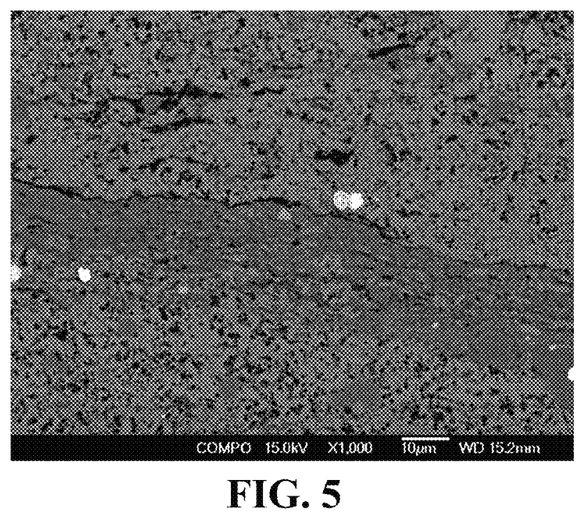
FIGS. 5 and 6 are high-resolution, backscatter electron images derived from closely spaced laminae in a rock sample.
Figure 6:
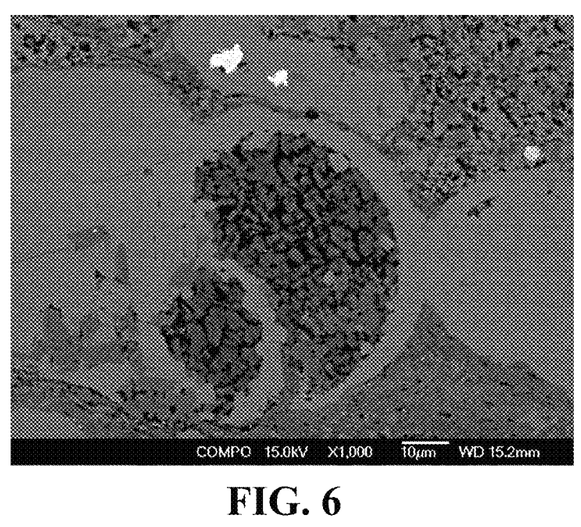

FIGS. 5 and 6 are high-resolution, backscatter electron images derived from closely spaced laminae in a rock sample. A comparison of the images of FIGS. 5 and 6 demonstrates the variability that can occur in the same rock sample. More particularly, these two images depict different laminae from the same rock sample, but have completely different connectivity, storage capacity, and wettability attributes. In FIG. 5, fine-grained laminae with clay mineral drape is observable in close association with fecal pellets. The intragranular porosity within the fecal pellets has been partly occluded by calcite and quartz cements. Despite the obvious cementation, relict intragranular pore space is still visible and contains a hydrocarbon phase.

In FIG. 6, coarse-grained laminae overlaying a clay mineral drape is observable. The coarse-grained lamina comprises foraminifer tests whose intragranular porosity has been mostly infilled by calcite cement. Quartz and kaolinite infill most of the residual intragranular porosity. The remnant intragranular porosity is infilled by a hydrocarbon phase.

Understanding the controls on the differences between the closely spaced laminae in the rock sample depicted in FIGS. 5 and 6 are important because they directly impact the storage capacity of the sediment and its geomechanical properties when it is being considered as an unconventional reservoir target. These analyses, however, have to take into account the lamina scale variability.

Figure 7:
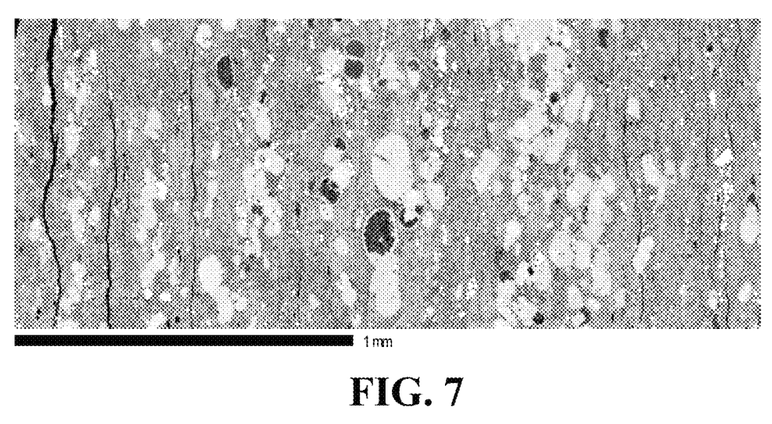
FIGS. 7 and 8 are high-resolution images of the fifth analysis region of FIG. 3.
Figure 8:
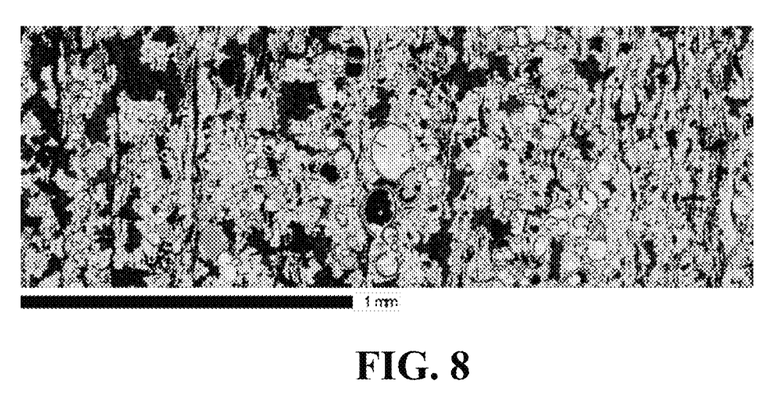

FIGS. 7 and 8 are high-resolution images of the fifth analysis region 310 of FIG. 3. An advantage of hyperspectral imaging is shown by comparing features resolved in FIG. 7 versus those in FIG. 8. FIG. 7 is a high-resolution backscatter electron image of the fifth analysis region 310, and FIG. 8 comprises a cathodoluminescent (CL) image of the fifth analysis region 310. The image of FIG. 7 contains information from backscattered electrons, obscuring some important features. FIG. 8 shows a particular spectral wavelength range near 346 nm. By adding large-field CL information, it is possible to distinguish between cements and grains in materials of similar composition, which are not discriminated in the backscatter electron image, and often not visible in x-ray compositional mapping. In contrast to what is shown here, conventional CL imaging is only capable of producing large-area images with image stitching methods and much longer acquisition times. Both of these are not viable, however, because long dwell times and overlap zones can result in beam damage to the sample and loss of CL signal.

In comparing FIGS. 7 and 8, it becomes readily apparent that some of the minerals present in the rock sample have different cathodoluminescent attributes. FIG. 8 essentially depicts a hyperspectral image or hyper-spectral data set comprising multiple frames that are stitched together (combined) using a computer. This technique allows a geologist to distinguish between grains and cement when mineralogy remains constant, which may be indicative of the ability for the rock to hydraulically fracture. Outline rimming of paleo grains, for example, is readily apparent in FIG. 8.

In some embodiments, the CL image may be displayed with a variety of colors, where each color indicates a different grain origin, a different cement type, porosity, etc. Moreover, the data can be processed to look at the energy of a specific x-ray, which may be indicative of a particular atomic element, and thus ascertain chemistry of the rock sample. For example, the computer may be programmed to color-code various atomic elements, e.g., red=iron (Fe), green=calcium (Ca), blue=aluminum (Al), etc. In other embodiments, however, the CL image may be produced or otherwise displaced with gray scale intensities rather than color. In such embodiments, the intensity of the signal may be proportional to the brightness of the gray scale value.

The high-resolution, multi-spectral images at pore/grain scale essentially provide a chemical map that can be analyzed to identify important rock sample features including, but not limited to, grain shape, grain size, grain location (distribution), porosity, intervening cements, composition of constituent materials, chemistry, mineralogy, mineral fabric, etc. More specifically, in the resulting high-resolution, multi-spectral image, there are multiple pixels, and each pixel contains information (e.g., BSI, EDS, WDS, CL, etc.). In some embodiments, an expert (e.g., a geologist) may analyze the multi-spectral images to identify the important rock sample features and link these features together into a statement about their likelihood of being a grain (e.g., a fine grain, a coarse grain, grain shape, etc.), a cement, a pore, etc. If all the grains are cemented together, that rock will likely be very strong and brittle causing it to fracture (fail) during hydraulic fracturing. If the grains are generally not cemented together, however, they will tend to slide past one another during hydraulic fracturing and "bend" instead of fracture with the rock being ductile.

As will be appreciated, pixel scale registration of the high-resolution data may facilitate automation of the manual task undertaken by a geologist of identifying the important rock sample features mentioned above. More specifically, computer software may be programmed to simultaneously process the high-resolution data for image object identification, and elemental and mineralogical mapping. Moreover, it may be possible to train (program) a computer to recognize the results from cathodoluminescence, e.g., all the material in red is a specific grain, cement, pore space, etc. In some embodiments, the high-resolution data may be processed using a combination of machine learning and coded image analysis, or alternatively this may be done with hard software code. This additional step automates the analysis to reveal more about the rock.

The present methods and systems may further include upscaling the high-resolution, multi-spectral image(s) relying on geolocation to place the high resolution data into a broader context through linkage to larger-scale features of the rock sample. More specifically, relying on the fact that each multi-spectral image has the same location in the rock sample, the higher-resolution images can be geo-located on larger-scale (lower-resolution) optical micrographs (e.g., FIG. 1). Moreover, it may be possible to further geo-locate the optical micrographs on the original hand specimen sized sample of the fine-grained rock. Geologists can use that data to determine what minerals are present in the sample, and what characteristic formation gave rise to the sample (representative of the subterranean formation rock). Pixel scale registration of the high-resolution data may also facilitate automation of upscaling the high-resolution, multi-spectral image(s) using a programmed computer.

Figure 9:
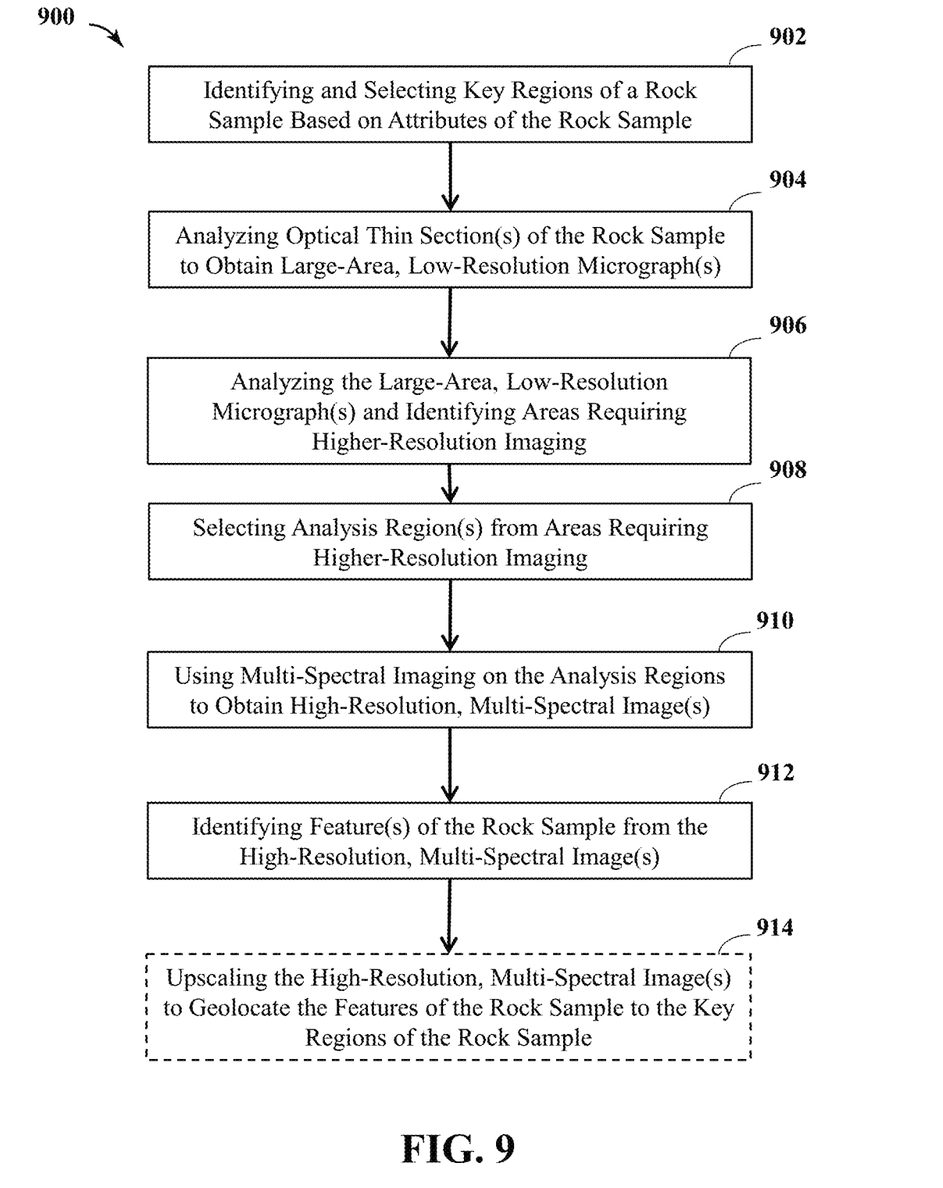
FIG. 9 is a schematic flow chart of an example method of analyzing fine-grained rock, according to one or more embodiments of the present disclosure.

FIG. 9 is a schematic flow chart of an example method 900 of analyzing fine-grained rock, according to one or more embodiments of the present disclosure. As illustrated, the method may commence by identifying and selecting one or more key regions of a rock sample based on one or more attributes of the rock sample, as at 902. Once the key regions have been identified and selected, one or more optical thin sections of the rock sample may be analyzed with low-resolution microscopy, and thereby obtain one or more low-scale micrographs, as at 904. The method 900 may further include analyzing the one or more low-scale micrographs and identifying areas requiring higher-resolution imaging, as at 906. One or more analysis regions may then be selected from the areas requiring higher-resolution imaging, as at 908, and multi-spectral imaging may be used on the one or more analysis regions to obtaining a corresponding one or more high-resolution, multi-spectral images, as at 910. One or more features of the rock sample may then be identified from the corresponding one or more high-resolution, multi-spectral images, as at 912. In some embodiments, the method 900 may optionally include upscaling the corresponding one or more high-resolution, multi-spectral images and thereby geo-locating the one or more features of the rock sample to the one or more key regions of the rock sample, as at 914.

The present disclosure describes or otherwise discloses components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, a special purpose computer, or other programmable data processing apparatus to produce a machine, such that the instructions that are executed on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method of analyzing of a rock sample, comprising:
    identifying and selecting one or more key regions of the rock sample based on one more attributes of the rock sample;
    analyzing one or more large-area, low-resolution micrographs of the rock sample obtained with large-area, low resolution microscopy and identifying and geo-locating areas requiring higher-resolution imaging, wherein the low-resolution microscopy comprises at least one of optical microscopy and low-magnitude backscatter election microscopy;
    selecting one or more analysis regions from the areas requiring higher-resolution imaging based on attributes of the areas requiring higher-resolution imaging;
    using multi-spectral imaging on the one or more analysis regions and thereby obtaining a corresponding one or more high-resolution, multi-spectral image;
    simultaneously processing the one or more high-resolution, multi-spectral image for object identification of rock sample features, and elemental and mineralogical mapping; and
    upscaling the corresponding one or more high-resolution, multi-spectral image and thereby geo-locating one or more features of the rock sample to the one or more key regions of the rock sample.

2. The method of claim 1, wherein analyzing the one or more large-area, low-resolution micrographs is receded by analyzing one or more optical thin sections of the rock sample with the large-area, low-resolution microscopy and thereby obtaining the one or more low-scale micrographs.

3. The method of claim 1, wherein selecting the one or more analysis regions further comprises selecting a multi-spectral imaging method based on at least one of a desired image resolution, a time required to obtain the desired image resolution, and a maximum data set size.

4. The method of claim 3, wherein the multi-spectral imaging method is selected from the group consisting of high-resolution backscattered electron imaging, energy dispersive x-ray spectroscopy, wavelength dispersive x-ray spectroscopy, high resolution x-ray fine structure spectroscopy, spectrally-resolved cathodoluminescence, pana-chromatic cathodoluminescent imaging, secondary electron imaging, energy-filtered secondary or backscattered electron imaging, angle-resolved electron imaging, magnetic domain imaging, electron-induced acoustic imaging, electron beam induced charge imaging, electron diffraction based imaging, electron-induced infrared imaging, fourier-transform infrared spectroscopy, ultraviolet imaging, atomic force microscopy imaging, and acoustic microscopy imaging.

5. The method of claim 3, wherein selecting the multi-spectral imaging method includes selecting a sequential order of analysis and is further based on a consideration of potential physical damage of the rock sample by prolonged exposure to electron beams.

6. The method of claim 1, wherein the one or more features of the rock sample are selected from the group consisting of grain shape, grain size, grain location, porosity, intervening cements, composition of pore lining materials, mineralogy, mineral fabric, and any combination thereof.

7. The method of claim 1, wherein the multi-spectral imaging comprises cathodoluminescence and the method further comprises:
obtaining a cathodoluminescent image;
identifying from the cathodluminescent image a property selected from the group consisting of grain origin, cement type, chemistry, and porosity; and
displaying the property using one or more colors or with gray scale intensity.

8. The method of claim 1, wherein identifying the one or more features of the rock sample is automated using a computer programmed to identify the one or more features of the rock sample.

9. The method of claim 1, wherein upscaling the corresponding one or more high-resolution, multi-spectral image is automated with a computer.

10. The method of claim 1, further comprising conducting a downhole hydraulic fracturing operation based on identification of the one or more features of the rock sample.

11. An apparatus, comprising:
one or more processors; and
a memory having embodied thereon processor executable instructions that, when executed by the one or more processors, cause the apparatus to:
identify and select one or more key regions of a rock sample based on one or more attributes of the rock sample;
analyze one or more optical thin sections of the rock sample with large-area, low resolution microscopy and thereby obtain one or more large-area, low-resolution micrographs, wherein the low-resolution microscopy comprises at least one of optical microscopy and low-magnitude backscatter electron microscopy;
analyze the one or more large-area, low-resolution micrographs and identifying areas requiring higher-resolution imaging;
select one or more analysis regions from the areas requiring higher-resolution imaging based on attributes of the areas requiring higher-resolution imaging;
use multi-spectral imaging on the one or more analysis regions and thereby obtain a corresponding one or more high-resolution, multi-spectral image;
simultaneously process the one or more high-resolution, multi-spectral image for object identification of rock sample features, and elemental and mineralogical mapping; and
upscale the corresponding one or more high-resolution, multi-spectral image and thereby geo-locate the one or more features of the rock sample to the one or more key regions of the rock sample.

12. The apparatus of claim 11, wherein the processor executable instructions that, when executed by the one or more processors, cause the apparatus to select one or more analysis regions, further comprises causing the processor to select a multi-spectral imaging method based on at least one of a desired image resolution, a time required to obtain the desired image resolution, and a maximum data set size.

13. The apparatus of claim 12, wherein the multi-spectral imaging method is selected from the group consisting of high-resolution backscattered electron imaging, energy dispersive x-ray spectroscopy, wavelength dispersive x-ray spectroscopy, high resolution x-ray fine structure spectroscopy, spectrally-resolved cathodoluminescence, pana-chromatic cathodoluminescent imaging, secondary electron imaging, energy-filtered secondary or backscattered electron imaging, angle-resolved electron imaging, magnetic domain imaging, electron-induced acoustic imaging, electron beam induced charge imaging, electron diffraction based imaging, electron-induced infrared imaging, fourier-transform infrared spectroscopy, ultraviolet imaging, atomic force microscopy imaging, and acoustic microscopy imaging.

14. The apparatus of claim 11, wherein the one or more features of the rock sample are selected from the group consisting of grain shape, grain size, grain location, porosity, intervening cements, composition of pore lining materials, mineralogy, mineral fabric, and any combination thereof.

15. The apparatus of claim 11, wherein the multi-spectral imaging comprises cathodoluminescence and wherein the processor executable instructions further cause the apparatus to:
obtain a cathodoluminescent image;
identify from the cathodluminescent image a property selected from the group consisting of grain origin, cement type, chemistry, and porosity; and
display the property using one or more colors or with gray scale.

16. The apparatus of claim 11, wherein the processor executable instructions that, when executed by the one or more processors, cause the apparatus to analyze the one or more large-area, low-resolution micrographs further comprises causing the processor to identify large-scale texture components.

* * * * *